United States Patent
Oba et al.

(10) Patent No.: US 10,537,922 B2
(45) Date of Patent: Jan. 21, 2020

(54) CLEANING APPARATUS, CLEANING METHOD, AND IMAGING APPARATUS

(71) Applicant: SONY CORPORATION, Tokyo (JP)

(72) Inventors: Eiji Oba, Tokyo (JP); Tooru Kihira, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 89 days.

(21) Appl. No.: 14/414,993

(22) PCT Filed: Jun. 5, 2013

(86) PCT No.: PCT/JP2013/065566
§ 371 (c)(1),
(2) Date: Jan. 15, 2015

(87) PCT Pub. No.: WO2014/017178
PCT Pub. Date: Jan. 30, 2014

(65) Prior Publication Data
US 2015/0202663 A1 Jul. 23, 2015

(30) Foreign Application Priority Data

Jul. 25, 2012 (JP) ................................ 2012-164981

(51) Int. Cl.
*H04N 5/217* (2011.01)
*B08B 5/00* (2006.01)
*H04N 5/225* (2006.01)

(52) U.S. Cl.
CPC ............. *B08B 5/00* (2013.01); *H04N 5/2251* (2013.01)

(58) Field of Classification Search
CPC ............. H04N 1/00909; H04N 1/4097; H04N 5/2171; G02B 27/0006
See application file for complete search history.

(56) References Cited

U.S. PATENT DOCUMENTS 5,708,859 A * 1/1998 Tajima ............... G02B 27/0006
348/E5.026
6,327,021 B1 * 12/2001 Higashiguchi ............ G03F 1/82
355/30
(Continued)

FOREIGN PATENT DOCUMENTS

JP 11027475 A * 1/1999
JP 2005-295152 10/2005
(Continued)

OTHER PUBLICATIONS

Title: Translation of JP 11027475 Author: Ohashi, Masakazu Date: Jan. 1999.*

(Continued)

*Primary Examiner* — Twyler L Haskins
*Assistant Examiner* — Wesley J Chiu
(74) *Attorney, Agent, or Firm* — Haug Partners LLP; William S. Frommer

(57) ABSTRACT

A determining unit 31 determines an image region of a foreign material in an imaged image generated by an imaging unit 22 by using an imaging optical system 21. A setting unit 32 sets a pressure, injection time, an injection direction of air injected to the foreign material, an injection pattern obtained by combining them and the like based on a determination result. A foreign material removal processing unit 33 adjusts air injection by an air injection adjusting unit 331 based on the setting by the setting unit 32 and injects from an air injecting unit 332 to the imaging optical system 21 to remove the foreign material adhering to the imaging optical system 21. The air is injected according to an adhesion condition of the foreign material, so that the foreign material adhering to the imaging optical system may be optimally removed.

10 Claims, 6 Drawing Sheets

(56) References Cited

U.S. PATENT DOCUMENTS

| | | | |
|---|---|---|---|
| 2004/0208395 A1* | 10/2004 | Nomura | G06T 5/20 382/275 |
| 2006/0268345 A1* | 11/2006 | Silverstein | G06T 7/001 358/3.26 |
| 2007/0159551 A1* | 7/2007 | Kotani | H04N 1/4097 348/349 |
| 2008/0192984 A1* | 8/2008 | Higuchi | G08G 1/16 382/104 |
| 2008/0198457 A1* | 8/2008 | Sakai | G02B 1/10 359/507 |
| 2008/0204565 A1* | 8/2008 | Yumiki | H04N 5/23219 348/208.99 |
| 2008/0285132 A1* | 11/2008 | O'Kane | G02B 27/0006 359/509 |
| 2009/0295944 A1* | 12/2009 | Tashiro | G03B 13/04 348/231.99 |
| 2010/0066890 A1* | 3/2010 | Ueda | G02B 7/102 348/333.02 |
| 2011/0266375 A1* | 11/2011 | Ono | B60S 1/0848 239/589 |
| 2012/0243093 A1* | 9/2012 | Tonar | G02B 27/0006 359/507 |
| 2013/0092758 A1* | 4/2013 | Tanaka | B60S 1/52 239/284.1 |
| 2013/0219742 A1* | 8/2013 | Field | B60S 1/0848 34/491 |
| 2015/0145956 A1* | 5/2015 | Hayakawa | B60S 1/56 348/46 |
| 2015/0172582 A1* | 6/2015 | Kiyohara | G06K 9/00791 348/322 |
| 2015/0203077 A1* | 7/2015 | Gokan | B60S 1/0848 134/36 |

FOREIGN PATENT DOCUMENTS

| | | |
|---|---|---|
| JP | 2006262242 A * | 9/2006 |
| JP | 2010-81273 | 4/2010 |
| JP | 2010-245786 | 10/2010 |
| JP | 2011-61390 | 3/2011 |
| JP | 2011-214612 | 10/2011 |

OTHER PUBLICATIONS

Title: Translation of JP2006-262242 Author: Nagamine, Takashi Date: Sep. 2006.*

Title: Sobel Filter Address: https://web.archive.org/web/20111002111145/https://en.wikipedia.org/wiki/Sobel_operator Date: Oct. 2, 2011 (Year: 2011).*

International Search Report issued in corresponding International Apiiication No. PCT/JP2013/065566.

First Office Action issued in corresponding Chinese Application No. 201380038080.3 dated Mar. 29, 2017 and its English Translation.

* cited by examiner

FIG. 3
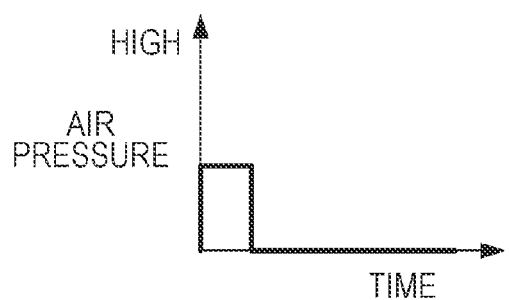
(A)
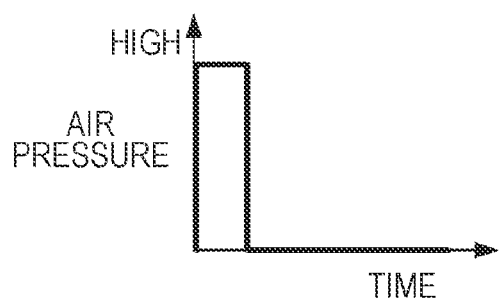
(B)
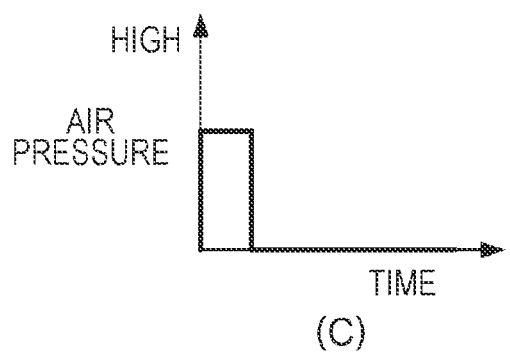
(C)
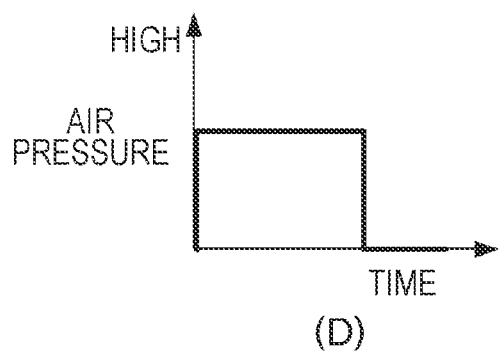
(D)
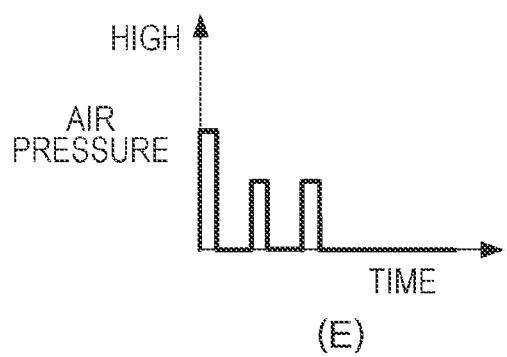
(E)
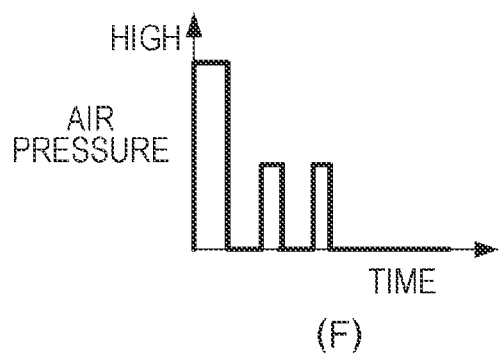
(F)

CLEANING APPARATUS, CLEANING METHOD, AND IMAGING APPARATUS

TECHNICAL FIELD

The technology relates to a cleaning apparatus, a cleaning method, and an imaging apparatus and enables optimal removal of a foreign material adhering to a lens of the imaging apparatus.

BACKGROUND ART

Conventionally, an imaging apparatus is mounted on a vehicle such as an automobile to use an image taken by the imaging apparatus in driving and the like. For example, a place seen with difficulty from a driver's seat is imaged such that a driver may easily recognize an obstacle and the like by using an in-vehicle monitor and the like. In addition, an area in front of a vehicle body is continuously imaged to avoid an accident or verify a situation when the accident occurs based on an imaged image. Furthermore, there also is a case in which the imaging apparatus is installed outside and the image taken by the imaging apparatus is used as evidence information of a crime.

When the imaging apparatus is installed outdoor or outside the vehicle, the imaging apparatus is exposed to the atmosphere and a foreign material such as a droplet and dust adheres to a lens portion and the like, thereby narrowing a field of view of the imaging apparatus or generating blurring and the like of the imaged image. Therefore, in Patent Document 1, it is determined whether the foreign material or the droplet adheres to the lens based on the image taken by the imaging apparatus to drive a wiper.

CITATION LIST

Patent Document

Patent Document 1: JP 2010-81273 A

SUMMARY OF THE INVENTION

Problems to be Solved by the Invention

In Patent Document 1, the wiper is driven according to whether the foreign material such as the droplet adheres to perform removal processing of the foreign material. Therefore, there might be a case in which the removal processing is not optimal according to an adhesion condition of the foreign material.

Therefore, an object of this technology is to provide a cleaning apparatus, a cleaning method, and an imaging apparatus capable of optimally removing a foreign material adhering to an imaging optical system.

Solutions to Problems

A first aspect of the present technology is
a cleaning apparatus including
a determining unit configured to determine an adhesion condition of a foreign material adhering to an imaging optical system,
a setting unit configured to set a foreign material removal operation based on a determination result of the determining unit, and
a foreign material removal processing unit configured to perform the foreign material removal operation based on the setting by the setting unit.

In this technology, the adhesion condition of the foreign material adhering to the imaging optical system is determined and the foreign material removal operation is set based on the determination result. For example, an image region of the foreign material in an imaged image generated by using the imaging optical system is determined and a pressure, injection time, and an injection direction of gas injected to the foreign material, an injection pattern obtained by combining them and the like are set based on the determination result. A frequency, amplitude, a waveform, and vibration time of vibration applied to a surface to which the foreign material adheres, a vibration pattern obtained by combining them and the like are set based on the determination result. The gas is injected to the foreign material and the vibration is applied to the surface to which the foreign material adheres and the foreign material removal operation is performed based on such settings based on the determination result. It is possible to easily determine and remove the adhered foreign material by giving a water-repellent property to the surface to which the foreign material adheres in the imaging optical system.

A second aspect of this technology is
a cleaning method including
a step of determining an adhesion condition of a foreign material adhering to a lens of an imaging apparatus,
a step of setting a foreign material removal operation based on a determination result of the adhesion condition, and
a step of performing the foreign material removal operation based on the setting.

A third aspect of this technology is
an imaging apparatus including
an imaging optical system,
an imaging unit configured to generate an image signal of an imaged image according to an optical image formed by the imaging optical system,
a determining unit configured to determine an adhesion condition of a foreign material adhering to the imaging optical system based on the image signal of the imaged image generated by the imaging unit,
a setting unit configured to set a foreign material removal operation based on a determination result of the determining unit, and
a foreign material removal processing unit configured to perform the foreign material removal operation based on the setting by the setting unit.

Effects of the Invention

According to this technology, the adhesion condition of the foreign material adhering to the imaging optical system is determined, the foreign material removal operation is set based on the determination result, and the foreign material removal operation is performed based on the setting. Therefore, it becomes possible to optimally remove the foreign material adhering to the imaging optical system. Meanwhile, an effect described in this specification is illustrative only and the effect is not limited to this, and there may be an additional effect.

BRIEF DESCRIPTION OF DRAWINGS

FIG. 3 is a view illustrating an air injection operation according to an adhesion condition of a foreign material.

MODE FOR CARRYING OUT THE INVENTION

Modes for carrying out the present technology are hereinafter described. Note that the description is given in the following order.
1. First Embodiment
1-1. Configuration of First Embodiment
1-2. Cleaning Operation of First Embodiment
2. Second Embodiment
2-2. Cleaning Operation of Second Embodiment 1. First Embodiment A case in which gas such as air is injected to remove a foreign material is described in a first embodiment.

[1-1. Configuration of First Embodiment]

Figure 1:
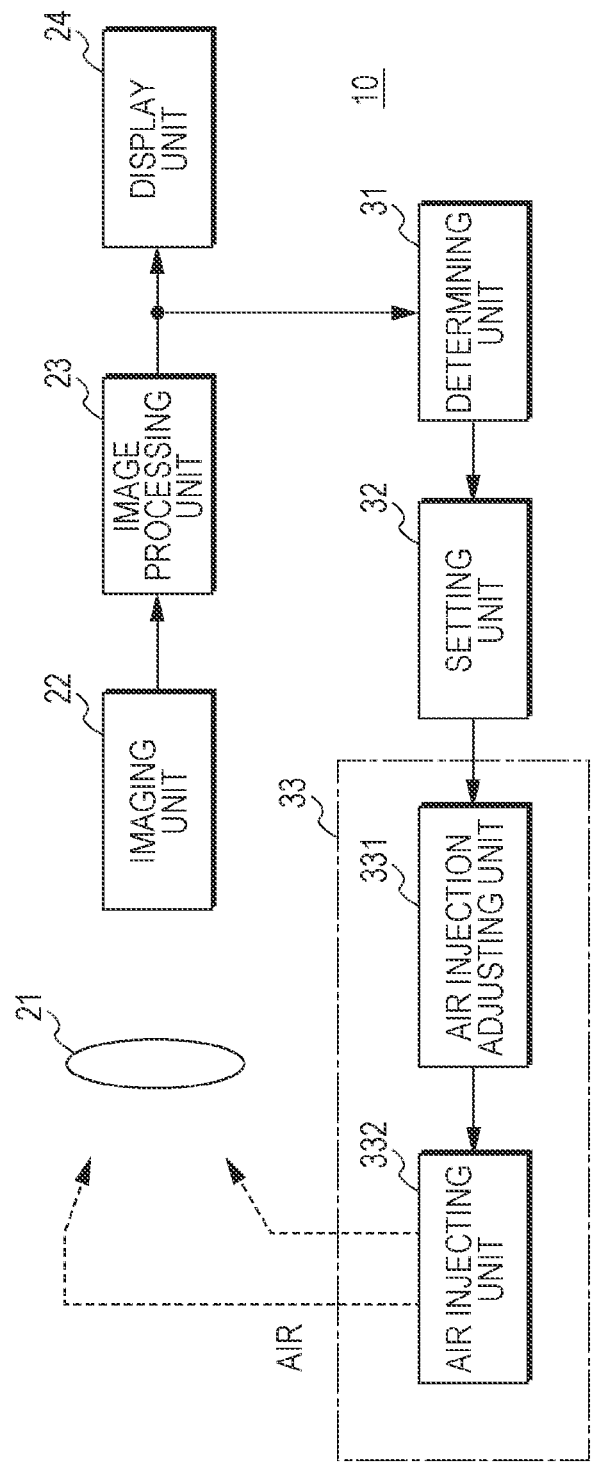
FIG. 1 is a view illustrating a configuration of a first embodiment.

FIG. 1 illustrates a configuration of the first embodiment of the present technology. An imaging apparatus 10 includes an imaging optical system 21, an imaging unit 22, an image processing unit 23, a display unit 24, a determining unit 31, a setting unit 32, and a foreign material removal processing unit 33.

The imaging optical system 21 formed of an imaging lens and the like forms an optical image of a subject on an imaging surface of the imaging unit 22.

The imaging unit 22 is formed of an imaging device such as a CCD (charge coupled device) image sensor and a CMOS (complementary metal-oxide semiconductor) image sensor. The imaging device performs photoelectric conversion processing to convert the optical image formed on the imaging surface by the imaging optical system 21 to an electric signal. The imaging unit 22 performs noise removal processing such as CDS (correlated double sampling), gain adjustment to set a level of the electric signal to a desired signal level, A/D conversion processing and the like on the electric signal generated by the imaging device. The imaging unit 22 outputs a digital image signal of an imaged image to the image processing unit 23.

The image processing unit 23 performs camera signal processing and the like on the digital image signal output from the imaging unit 22. The image processing unit 23 performs non-linear processing such as gamma correction and knee correction, color correction processing, a contour emphasis processing and the like on the image signal, for example. The image processing unit 23 outputs the processed image signal to the display unit 24 and the determining unit 31.

The display unit 24 displays the imaged image based on the image signal output from the image processing unit 23.

The determining unit 31 determines an adhesion condition of the foreign material adhering to a front surface of the imaging optical system 21. The determining unit 31 extracts a contour of an imaged object based on the image signal of the imaged image to determine whether the extracted contour corresponds to a contour of the foreign material. For example, the determining unit 31 stores a size of a contour of a droplet supposed to adhere to the imaging optical system 21 in advance and compares a size of the extracted contour with the stored size of the contour to determine that the contour smaller than the stored contour is that of the droplet. The determining unit 31 may determine the foreign material based on not only the size of the contour of the object but also a shape of the contour, luminance and a color, blurring and distortion of the image and the like. The determining unit 31 outputs information indicating an image region size of the determined foreign material to the setting unit 32 as a determination result. It is possible to calculate the region size by counting the number of pixels in a region determined to be the droplet or by approximating the region by a circle to use an area calculated from a diameter (radius or diameter) of the circle, for example. Meanwhile, it is possible to make the region of the droplet more similar to the circle by giving a water-repellent property to the surface to which the foreign material adheres, thereby accurately and easily calculating the region size and determining the foreign material. It becomes easy to remove the droplet by giving the water-repellent property to the surface to which the foreign material adheres. Furthermore, when a plurality of image regions of the foreign materials is determined, the determining unit 31 may add up the determined regions to obtain the image region size of the foreign material.

The setting unit 32 sets a foreign material removal operation based on the determination result of the determining unit 31. When the foreign material removal processing unit 33 injects the air to perform the foreign material removal operation, the setting unit 32 sets a pressure and/or injection time and the like of the air to be injected and outputs setting information to the foreign material removal processing unit 33.

The foreign material removal processing unit 33 includes an air injection adjusting unit 331 and an air injecting unit 332. The air injection adjusting unit 331 allows the air injecting unit 332 to inject the air at the pressure and/or the injection time and the like indicated by the setting information supplied from the setting unit 32 to remove the foreign material adhering to the front surface of the imaging optical system 21.

[1-2. Cleaning Operation of First Embodiment]

Figure 2:
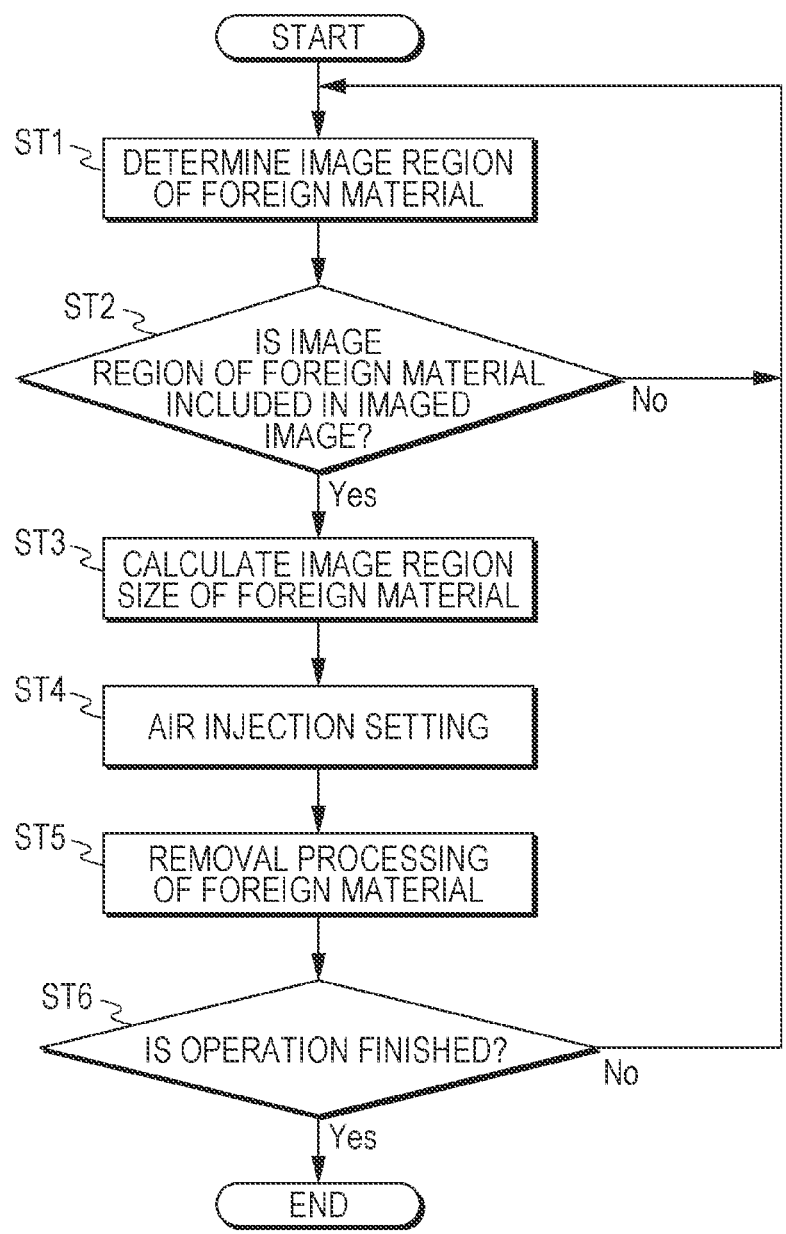
FIG. 2 is a flowchart illustrating a cleaning operation of the first embodiment.

FIG. 2 is a flowchart illustrating a cleaning operation of the first embodiment. At step ST1, the determining unit 31 determines the image region of the foreign material in the imaged image. The determining unit 31 determines the image region of the foreign material by using the image signal supplied from the image processing unit 23. The determining unit 31 extracts the contour and determines the droplet and the like based on the size of the extracted contour, for example. Meanwhile, the determining unit 31 may also determine the foreign material based on the shape of the contour, the luminance and the color, the blurring and the distortion of the image and the like. The determining unit 31 determines the image region of the foreign material and shifts to step ST2.

At step ST2, the determining unit 31 determines whether the image region of the foreign material is included in the imaged image. The determining unit 31 shifts to step ST3 when the image region of the foreign material is included and returns to step ST1 when the image region of the foreign material is not included.

At step ST3, the determining unit 31 calculates the image region size of the foreign material. The determining unit 31 calculates the image region size of the foreign material such as the number of pixels in the image region of the foreign material and shifts to step ST4.

At step ST4, the setting unit 32 configures an air injection setting. The setting unit 32 sets the pressure and/or the injection time of the air to be injected based on the region size calculated at step ST3. For example, the pressure is increased or the injection time is lengthened as the region size becomes larger such that the foreign material may be more surely removed. The setting unit 32 configures the air injection setting in this manner and shifts to step ST5.

At step ST5, the foreign material removal processing unit 33 performs removal processing of the foreign material. The foreign material removal processing unit 33 injects the air to the foreign material based on the air injection setting at step ST4 to remove the adhering foreign material and shifts to step ST6.

At step ST6, the imaging apparatus 11 determines whether the operation is finished. When the imaging apparatus 11 is mounted on a vehicle such as an automobile, for example, the imaging apparatus 11 determines that the operation is finished when driving is finished to finish the cleaning operation. During the driving, the imaging apparatus 11 determines that the operation is not finished and returns to step ST1.

In this manner, it is possible to efficiently remove the foreign material without wasting by adjusting the pressure and/or the injection time of the air to be injected according to the adhesion condition of the foreign material.

FIG. 3 illustrates an air injection operation according to the adhesion condition of the foreign material. When the pressure of the air to be injected is adjusted according to the adhesion condition of the foreign material, the setting unit 32 increases the pressure as the image region size of the foreign material becomes larger. For example, the setting unit 32 changes the pressure linearly with respect to the image region size (area of the image region) of the foreign material. Therefore, the pressure of the air is set low as illustrated in FIG. 3A when the image region size of the foreign material is small and the pressure of the air is set higher as illustrated in FIG. 3B as the image region size of the foreign material becomes larger.

When the injection time of the air to be injected is adjusted according to the adhesion condition of the foreign material, the setting unit 32 lengthens the injection time as the image region size of the foreign material becomes larger. Therefore, the air injection time is set short as illustrated in FIG. 3C when the image region size of the foreign material is small and the air injection time is set longer as illustrated in FIG. 3D as the image region size of the foreign material becomes larger.

Furthermore, it is also possible to switch an injection pattern obtained by combining the pressure and the injection time of the air according to the adhesion condition of the foreign material. For example, when the image region size of the foreign material is small, the injection pattern illustrated in FIG. 3E is used, and when the image region size of the foreign material is large, the injection pattern illustrated in FIG. 3F is used. If the pressure is set high at an initial stage of the injection to decrease thereafter, the foreign material is more effectively removed. In this manner, by switching the injection pattern according to the adhesion condition of the foreign material, it is possible to further efficiently remove the foreign material without wasting. Meanwhile, the injection patterns in FIGS. 3E and 3F are illustrative only and the injection pattern is not limited to those illustrated in the drawings.

In a configuration in which an injection direction of the air may be controlled, it is possible to set the injection direction of the air and the pressure and the injection time for each injection direction according to the adhesion condition of the foreign material. For example, when a nozzle which may change the injection direction of the air is used, or when a plurality of nozzles with different injection directions of the air is provided, for example, it is possible to set the injection pattern including the injection direction of the air to switch the injection pattern according to the adhesion condition of the foreign material.

In this case, it is possible to divide the image region of the foreign material into a plurality of regions and set the injection pattern for each region or to set the injection pattern for each of the determined foreign materials. It is possible to inject the air from the nozzle the closest to the adhering foreign material to remove the same, for example, by setting in this manner. It is also possible to remove the foreign material which cannot be removed by the air from the nozzle the closest to the foreign material by the air injected from another direction by injecting the air from another nozzle thereafter.

2. Second Embodiment

A case in which vibration is applied to a surface to which a foreign material adheres to remove the foreign material is described in a second embodiment.

[2-1. Configuration of Second Embodiment]

Figure 4:
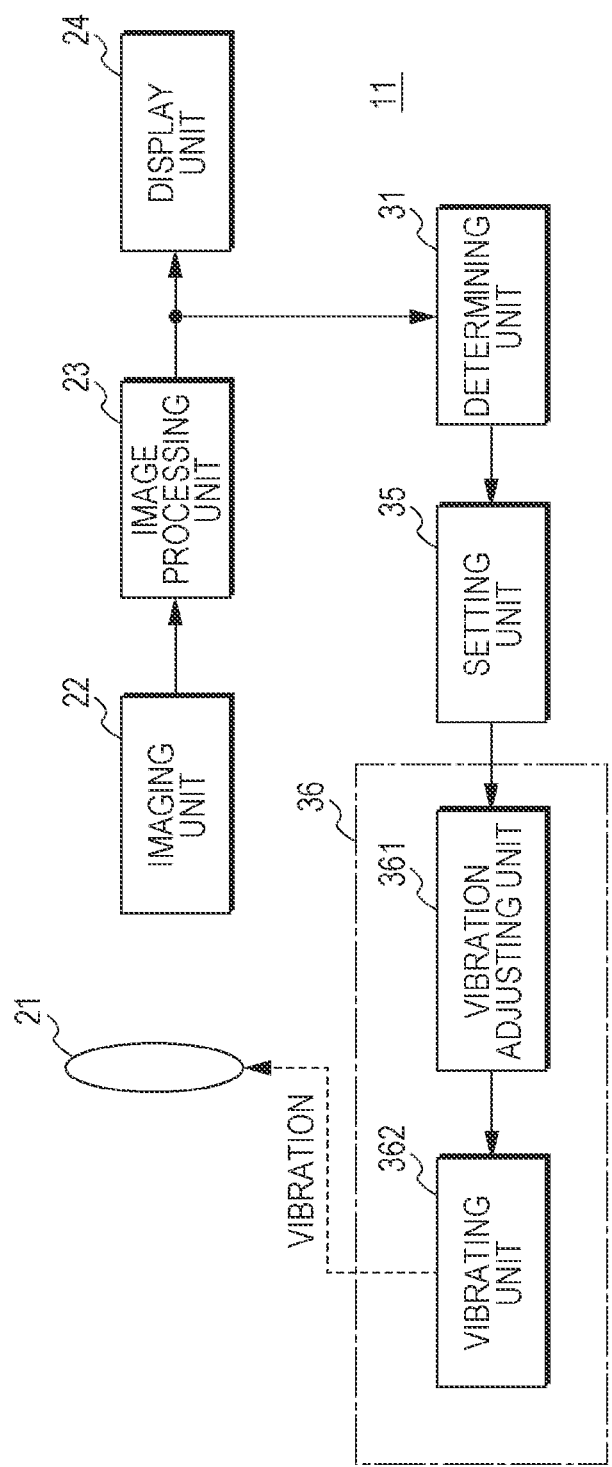
FIG. 4 is a view illustrating a configuration of a second embodiment.

FIG. 4 illustrates a configuration of the second embodiment of the present technology. An imaging apparatus 10 includes an imaging optical system 21, an imaging unit 22, an image processing unit 23, a display unit 24, a determining unit 31, a setting unit 35, and a foreign material removal processing unit 36.

The imaging optical system 21 formed of an imaging lens and the like forms an optical image of a subject on an imaging surface of the imaging unit 22.

The imaging unit 22 is formed of an imaging device such as a CCD (charge coupled device) image sensor and a CMOS (complementary metal-oxide semiconductor) image sensor. The imaging device performs photoelectric conversion processing to convert the optical image formed on the imaging surface by the imaging optical system 21 to an electric signal. The imaging unit 22 performs noise removal processing such as CDS (correlated double sampling), gain adjustment to set a level of the electric signal to a desired signal level, A/D conversion processing and the like on the electric signal generated by the imaging device. The imaging unit 22 outputs a digital image signal of an imaged image to the image processing unit 23.

The image processing unit 23 performs camera signal processing and the like on the digital image signal output from the imaging unit 22. The image processing unit 23 performs non-linear processing such as gamma correction and knee correction, color correction processing, contour emphasis processing and the like on the image signal, for example. The image processing unit 23 outputs the processed image signal to the display unit 24 and the determining unit 31.

The display unit 24 displays the imaged image based on the image signal output from the image processing unit 23.

The determining unit 31 determines an adhesion condition of the foreign material adhering to a front surface of the imaging optical system 21. The determining unit 31 extracts a contour of an imaged object based on the image signal of the imaged image to determine whether the extracted contour corresponds to a contour of the foreign material. For example, the determining unit 31 stores a size of a contour of a droplet supposed to adhere to the imaging optical system 21 in advance and compares a size of the extracted contour with the stored size of the contour to determine that the contour smaller than the stored contour is that of the droplet. The determining unit 31 may determine the foreign material based on not only the size of the contour of the object but also a shape of the contour, luminance and a color, blurring and distortion of the image and the like. The determining unit 31 outputs information indicating an image region size of the determined foreign material to the setting unit 32 as a determination result. A method of calculating the region size is similar to that of the first embodiment. It becomes easy to determine and remove the adhering foreign material as described above by giving a water-repellent property to the surface to which the foreign material adheres. When a plurality of image regions of the foreign materials is determined, the determining unit 31 may add up the determined regions to obtain the image region size of the foreign material.

The setting unit 35 sets a foreign material removal operation based on the determination result of the determining unit 31. When the foreign material removal processing unit 36 applies the vibration to the surface to which the foreign material adheres to perform the foreign material removal operation, the setting unit 35 sets a frequency, amplitude, vibration time and the like of the vibration, for example, and outputs setting information to the foreign material removal processing unit 36.

The foreign material removal processing unit 36 includes a vibration adjusting unit 361 and a vibrating unit 362. The vibration adjusting unit 361 allows the vibrating unit 362 to vibrate the surface to which the foreign material adheres at the frequency, the amplitude, the vibration time and the like indicated by the setting information supplied from the setting unit 32 to remove the foreign material adhering to the front surface of the imaging optical system 21. Meanwhile, the vibrating unit 362 is formed of a piezoelectric device and the like and mounted so as to be vibrate the front surface to which the foreign material adheres in the imaging optical system 21. For example, in the imaging optical system 21, if a lens cover and a lens protector are provided on the front surface of the imaging lens and when the foreign material adheres to the lens cover and the lens protector, the vibrating unit 362 is provided thereon.

[2-2. Cleaning Operation of Second Embodiment]

Figure 5:
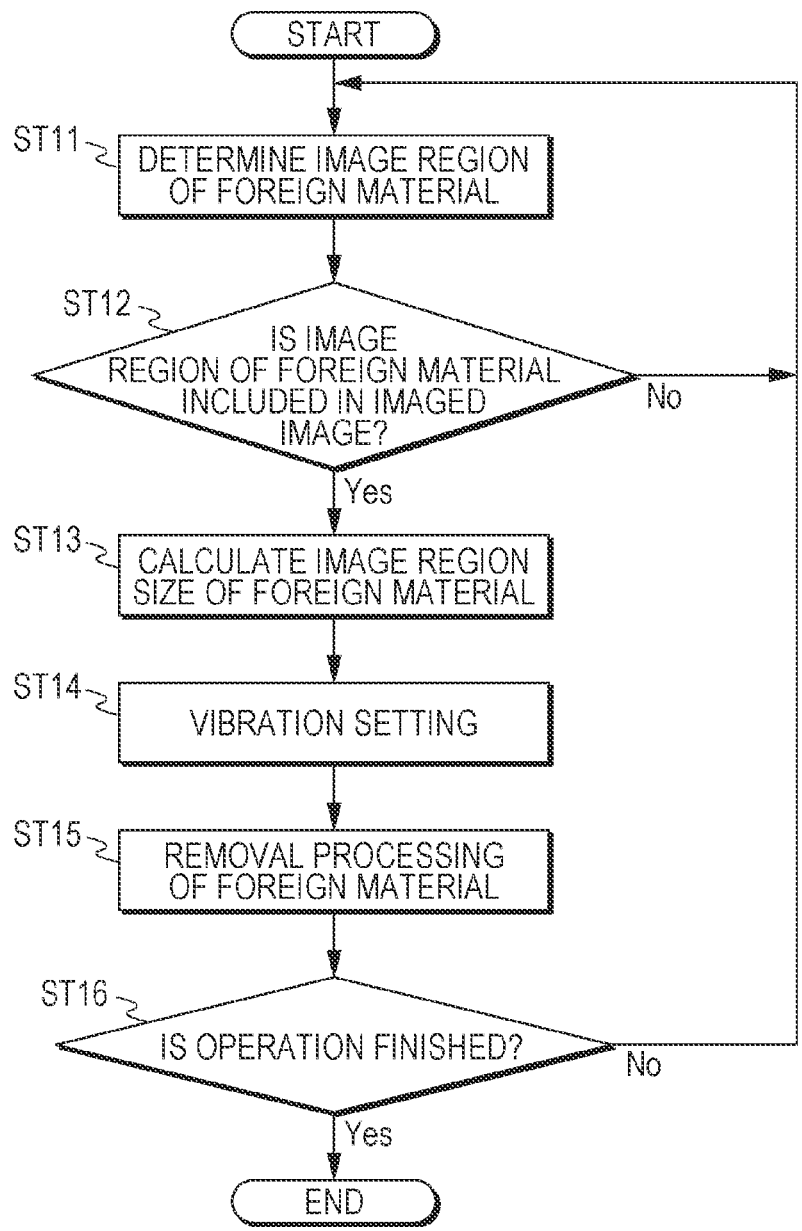
FIG. 5 is a flowchart illustrating a cleaning operation of the second embodiment.

FIG. 5 is a flowchart illustrating a cleaning operation of the second embodiment. At step ST11, the determining unit 31 determines the image region of the foreign material in the imaged image. The determining unit 31 determines the image region of the foreign material by using the image signal supplied from the image processing unit 23. The determining unit 31 extracts the contour and determines the droplet and the like based on the size of the extracted contour, for example. Meanwhile, the determining unit 31 may determine the foreign material based on the shape of the contour, the luminance and the color, the blurring and the distortion of the image and the like. The determining unit 31 determines the image region of the foreign material and shifts to step ST12.

At step ST12, the determining unit 31 determines whether the image region of the foreign material is included in the imaged image. The determining unit 31 shifts to step ST13 when the image region of the foreign material is included and returns to step ST11 when the image region of the foreign material is not included.

At step ST13, the determining unit 31 calculates the image region size of the foreign material. The determining unit 31 calculates the image region size of the foreign material such as the number of pixels in the image region of the foreign material and shifts to step ST14.

At step ST14, the setting unit 35 configures a vibration setting. The setting unit 35 sets the frequency, the amplitude, the vibration time and the like of the vibration applied to the surface to which the foreign material adheres based on the region size calculated at step ST13. For example, the amplitude is increased and the vibration time is lengthened as the region size becomes larger such that the foreign material may be more surely removed. The setting unit 35 configures the vibration setting in this manner and shifts to step ST15.

At step ST15, the foreign material removal processing unit 36 performs removal processing of the foreign material. The foreign material removal processing unit 36 vibrates the surface to which the foreign material adheres to remove the adhering foreign material based on the vibration setting at step ST14 and shifts to step ST16.

At step ST16, the imaging apparatus 11 determines whether the operation is finished. When the imaging apparatus 11 is mounted on a vehicle such as an automobile, for example, the imaging apparatus 11 determines that the operation is finished when driving is finished to finish the cleaning operation. During the driving, the imaging apparatus 11 determines that the operation is not finished to return to step ST11.

In this manner, it is possible to efficiently remove the foreign material without wasting by adjusting the frequency, the amplitude, and the vibration time of the vibration applied to the surface to which the foreign material adheres according to the adhesion condition of the foreign material.

Figure 6:
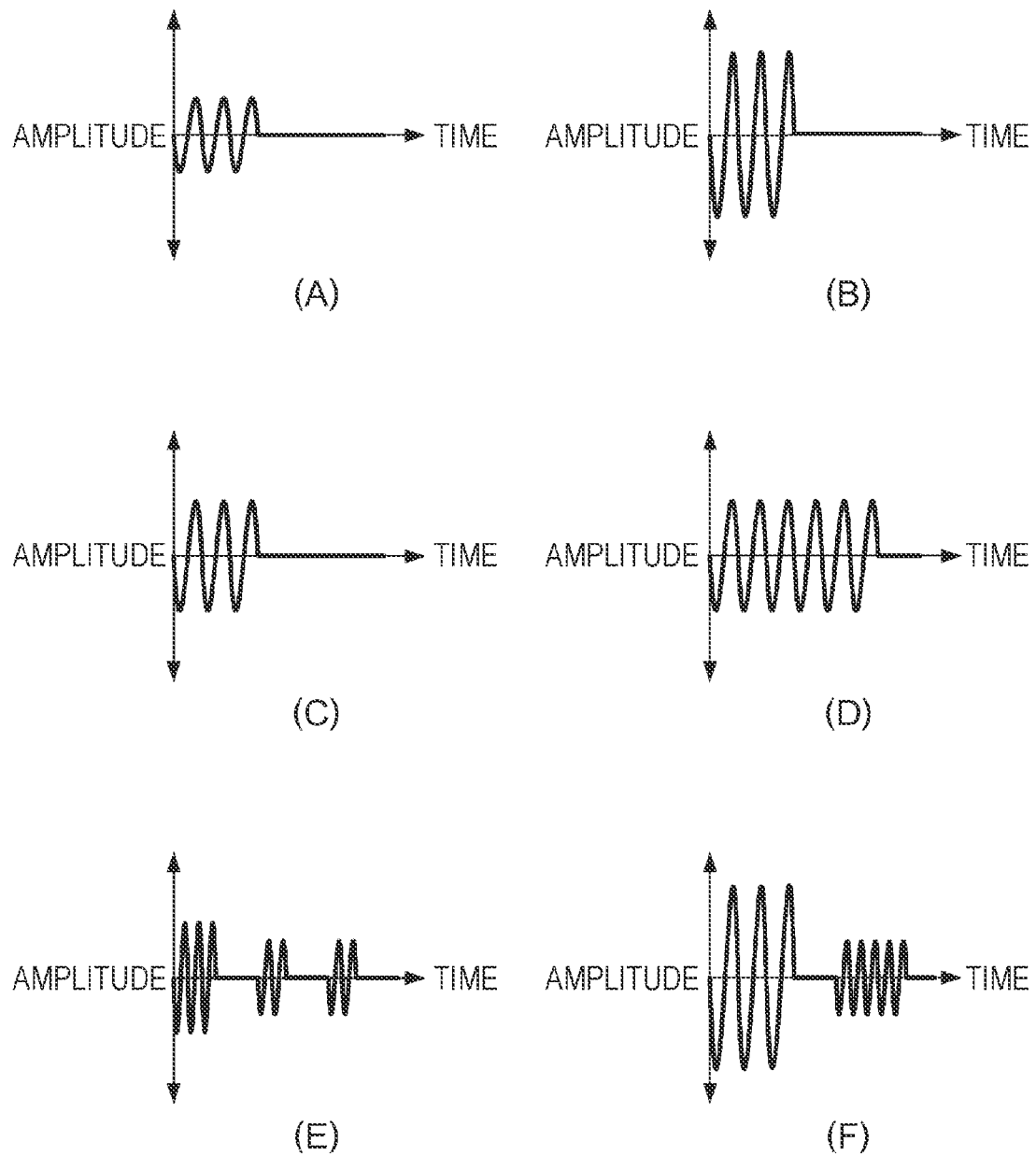
FIG. 6 is a view illustrating a vibration operation according to an adhesion condition of a foreign material.

FIG. 6 illustrates a vibration operation according to the adhesion condition of the foreign material. Meanwhile, when the vibration operation according to the adhesion condition of the foreign material is performed, it is difficult to apply the different vibrations to respective parts of the surface to which the foreign material adheres. Therefore, the vibration is set by using a sum of the image region sizes of the foreign materials calculated by the determining unit 31.

When the amplitude is adjusted according to the adhesion condition of the foreign material, the setting unit 35 increases the amplitude as the image region size of the foreign material becomes larger. Therefore, the amplitude is set small as illustrated in FIG. 6A when the image region size of the foreign material is small and the amplitude is set larger as illustrated in FIG. 6B as the image region size of the foreign material becomes larger.

When the vibration time is adjusted according to the adhesion condition of the foreign material, the setting unit 32 lengthens the vibration time as the image region size of the foreign material becomes larger. Therefore, the vibration time is set short as illustrated in FIG. 6C when the image region size of the foreign material is small and the vibration time is set longer as illustrated in FIG. 6D as the image region size of the foreign material becomes larger.

Furthermore, it is also possible to adjust the frequency and a waveform of the vibration according to the adhesion condition of the foreign material and to switch a vibration pattern obtained by combining the amplitude, the frequency, the waveform, and the vibration time according to the adhesion condition of the foreign material. For example, when the image region size of the foreign material is small, the vibration pattern illustrated in FIG. 6E is used, and when the image region size of the foreign material is large, the vibration pattern illustrated in FIG. 6F is used. If the amplitude is set large at an initial stage of the vibration to decrease thereafter, the foreign material is more effectively removed. In this manner, it is possible to further efficiently remove the foreign material without wasting by switching the vibration pattern according to the adhesion condition of the foreign material. Meanwhile, the vibration patterns in FIGS. 6E and 6F are illustrative only and the vibration pattern is not limited to those illustrated in the drawings.

The present technology should not be interpreted so as to be limited to the above-described embodiments of the technology. The embodiments of the technology disclose the present technology as illustration and it is obvious that one skilled in the art may modify or replace the embodiments without departing from the scope of the present technology. That is to say, in order to determine the scope of the present technology, claims should be taken into consideration.

The cleaning apparatus of the present technology may also have the following configuration.

(1) A cleaning apparatus including:
a determining unit configured to determine an adhesion condition of a foreign material adhering to an imaging optical system;
a setting unit configured to set a foreign material removal operation based on a determination result of the determining unit; and
a foreign material removal processing unit configured to perform the foreign material removal operation based on the setting by the setting unit.

(2) The cleaning apparatus according to (1), wherein the determining unit determines an image region of the foreign material in an imaged image generated by the imaging apparatus as the adhesion condition.

(3) The cleaning apparatus according to (1) or (2), wherein the foreign material removal processing unit performs the foreign material removal operation by injecting gas.

(4) The cleaning apparatus according to (3), wherein the setting unit sets a pressure or injection time of the gas according to the adhesion condition of the foreign material determined by the determining unit.

(5) The cleaning apparatus according to (4), wherein the setting unit switches an injection pattern of the gas according to the adhesion condition of the foreign material determined by the determining unit.

(6) The cleaning apparatus according to any one of (3) to (5), wherein the foreign material removal processing unit injects the gas from different directions to the imaging optical system, and the setting unit sets an injection direction of the gas to the foreign material according to the adhesion condition of the foreign material determined by the determining unit.

(7) The cleaning apparatus according to any one of (1) to (6), wherein the foreign material removal processing unit performs the foreign material removal operation by applying vibration to a surface to which the foreign material adheres.

(8) The cleaning apparatus according to (7), wherein the setting unit sets a frequency, amplitude, a waveform, or vibration time of the vibration according to the adhesion condition of the foreign material determined by the determining unit.

(9) The cleaning apparatus according to (8), wherein the setting unit switches a vibration pattern of the vibration according to the adhesion condition of the foreign material determined by the determining unit.

(10) The cleaning apparatus according to any one of (1) to (9), wherein the surface to which the foreign material adheres in the imaging optical system has a water-repellent property.

INDUSTRIAL APPLICABILITY

In a cleaning apparatus, a cleaning method, and an imaging apparatus of this technology, an adhesion condition of a foreign material adhering to an imaging optical system is determined. A foreign material removal operation is set based on a determination result and the foreign material removal operation is performed based on the setting. Therefore, it becomes possible to optimally remove the foreign material adhering to the imaging optical system. Therefore, the cleaning apparatus, the cleaning method, and the imaging apparatus of this technology are suitable for the imaging apparatus in which the foreign material such as a droplet adheres to the imaging optical system, for example, an in-vehicle camera, a monitoring camera and the like.

REFERENCE SIGNS LIST 10, 11 imaging apparatus
21 imaging optical system
22 imaging unit
23 image processing unit
24 display unit
31 determining unit
32, 35 setting unit
33, 36 foreign material removal processing unit
331 air injection adjusting unit
332 air injecting unit
361 vibration adjusting unit
362 vibrating unit

The invention claimed is:

1. A cleaning apparatus comprising:
an injector configured to perform a foreign material removal operation to remove foreign material adhering to a surface by injecting gas; and
processing circuitry configured to:
acquire a digital image signal representing an image formed to remove foreign material adhering to a surface by an imaging unit;
perform contour emphasis processing on the digital image signal;
extract a contour of an imaged object based upon the image signal;
determine that the imaged object corresponds to a foreign material adhering to the surface of an imaging lens of the imaging unit based on a shape or size of the extracted contour;
determine an adhesion condition of the foreign material adhering to the imaging lens based upon the determination; and
set a foreign material removal operation based on a determination result of the processing circuitry;
wherein the injector is configured to perform the foreign material removal operation based on the setting by the processing circuitry;
wherein the processing circuitry modifies a non-zero gas injection pressure of the injector according to the determined adhesion condition by switching from a first gas injection pattern to a second gas injection pattern according to the determined adhesion condition of the foreign material;
wherein the first and the second gas injection pattern each comprises a plurality of pulses, with a first pulse of the plurality of pulses having a greater pressure than at least one subsequent pulse; and
wherein the surface of the imaging lens has a water-repellent property.

2. The cleaning apparatus according to claim 1, wherein the processing circuitry determines an image region of the foreign material in the image generated by using the imaging unit.

3. The cleaning apparatus according to claim 1, wherein the processing circuitry further sets an injection time of the gas according to the adhesion condition of the foreign material determined by the processing circuitry.

4. The cleaning apparatus according to claim 1, wherein the first pulse of the first gas injection pattern has a pressure that is different than the first pulse of the second gas injection pattern.

5. The cleaning apparatus according to claim 1, wherein the injector injects the gas from different directions to the imaging lens, and
the processing circuitry sets an injection direction of the gas to the foreign material according to the adhesion condition of the foreign material determined by the processing circuitry.

6. A cleaning method comprising:
a step acquiring a digital image signal representing an image formed by an imaging unit;
a step of performing contour emphasis processing on the digital image signal;
a step of extracting a contour of an imaged objet based upon the image signal;
a step of determining that the imaged object corresponds to a foreign material adhering to a surface of an imaging lens of the imaging unit based on a shape or size of the extracted contour,
a step of determining an adhesion condition of the foreign material adhering to the surface of the imaging lens based upon the determination,
a step of setting a foreign material removal operation based on a determination result of the adhesion condition, wherein the setting comprises modifying a non-zero gas injection pressure according to the determined result of the adhesion condition by switching from a first gas injection pattern to a second gas injection pattern according to the determined adhesion condition of the foreign material, wherein the first and the second gas injection pattern each comprises a plurality of pulses, with a first pulse of the plurality of pulses having a greater pressure than at least one subsequent pulse, and
a step of performing the foreign material removal operation based on the setting,
wherein the surface of the imaging lens has a water-repellent property.

7. An imaging apparatus comprising:
an imaging optical system including an imaging lens,
an imaging unit configured to generate an image signal of an imaged image according to an optical image formed by the imaging optical system,
an injector configured to perform a foreign material removal operation by injecting gas, and
processing circuitry configured to:
  acquire the image signal;
  perform contour emphasis processing on the image signal;
  extract a contour of an imaged object based upon the image signal;
  determine that the imaged object corresponds to a foreign material adhering to a surface of the imaging lens in the image signal based on a shape or size of the extracted contour;
  determine an adhesion condition of the foreign material adhering to the imaging lens of the imaging optical system based on the determination, and
  set a foreign material removal operation based on a determination result of the processing circuitry;
wherein the injector is configured to perform the foreign material removal operation based on the setting by the processing circuitry;
wherein the processing circuitry modifies a non-zero gas injection pressure of the injector according to the determined adhesion condition by switching from a first gas injection pattern to a second gas injection pattern according to the determined adhesion condition of the foreign material;
wherein the first and the second gas injection pattern each comprises a plurality of pulses, with a first pulse of the plurality of pulses having a greater pressure than at least one subsequent pulse, and
wherein the surface of the imaging lens has a water-repellent property.

8. The cleaning apparatus according to claim 1, wherein determining the adhesion condition of the foreign material adhering to the imaging lens comprises comparing the extracted contour to a reference contour.

9. The cleaning method according to claim 6, wherein the step of determining the adhesion condition of the foreign material adhering to the imaging lens comprises comparing the extracted contour to a reference contour.

10. The imaging apparatus according to claim 7, wherein determining the adhesion condition of the foreign material adhering to the imaging lens comprises comparing the extracted contour in the imaging signal of the imaged image generated by the imaging unit with a reference contour.

* * * * *